United States Patent [19]

Herman et al.

[11] Patent Number: 5,062,998

[45] Date of Patent: Nov. 5, 1991

[54] PREPARATION OF METALLATED AND SUBSTITUTED ALKYNES

[75] Inventors: Frederick L. Herman, Allentown; Ann C. L. Savoca, Sinking Spring; Mark L. Listemann, Whitehall, all of Pa.

[73] Assignee: Air Products and Chemicals, Inc., Allentown, Pa.

[21] Appl. No.: 513,133

[22] Filed: Apr. 23, 1990

[51] Int. Cl.$^5$ .......................... C07F 1/02; C07F 1/04; C07F 1/06; C07F 1/00

[52] U.S. Cl. ................................ 260/665 R; 585/534; 585/538

[58] Field of Search .................................. 260/665 R

[56] References Cited

U.S. PATENT DOCUMENTS

| | | | |
|---|---|---|---|
| 3,410,918 | 11/1968 | Beumel, Jr. et al. | 260/665 |
| 3,671,605 | 6/1972 | Smith, Jr. | 260/678 |
| 3,752,848 | 8/1973 | Smith, Jr. | 260/526 N |
| 3,950,446 | 4/1976 | Gardner et al. | 260/665 R |
| 3,975,453 | 8/1976 | Smith | 260/665 R |
| 4,036,904 | 7/1977 | Strope | 260/681.5 R |
| 4,060,567 | 11/1977 | Taguma et al. | 260/665 R X |
| 4,339,397 | 7/1982 | Ishihara et al. | 260/665 R |
| 4,526,720 | 7/1985 | Van Rheeven et al. | 260/665 R X |

OTHER PUBLICATIONS

Z. L. Dykh et al., "In Spectra of Catalysts and Adsorbed Molecules 25, Isomerization of Allene and Methylacetylene on Aluminum Oxide," Izv. Akad., Nauk. SSSR, Ser. Khim (1978) 11, 2473.

C. P. Khulbe et al., "Allene-Methylacetylene Isomerization over Silica-Supported Cobalt and Iron Catalysts", Canadian Journal of Chemistry, vol. 56, No. 22, Nov. 15, 1978, p. 2791.

C. A. Brown et al., "The Acetylene Zipper, an Exceptionally Facile 'Contrathermodynamic' Multipositional Isomerization of Alkynes with Potassium 3-Aminopropylamide," J. Am. Chem. Soc., p. 891 (1975) 97.

S. R. MaCaulay, "The rearrangement of Isomeric Linear Decyn-1-ols by Reaction with the Sodium Salt of 1,3-diaminopropane," Can. J. Chem., 1980, National Research Council of Canada, p. 2567, 58.

S. R. Abrams, "Alkyne Isomerization Reagents: Alkal Metal Amides", Can. J. Chem., vol. 62, p. 1333 (1984).

S. R. Abrams "Isomerization of Acetylenic Acids with Sodium Salt of 1,2-Diamino-Ethane: A One Step Synthesis of Megatomoic Acid", Can. of Chem., p. 1238, (1984) 62.

J. H. Wotiz et al., "The Mechanism of the Base-Catalyzed Prototropic Propargylic Rearrangement in Vicinal Diamins", J. Org. Chem., vol. 38, No. 3, 1973, p. 489.

S. R. Abrams et al., "On the Mechanism of 1,3-Prototropic Shifts in Acetylene-Allene Isomerizations," J. Org. Chem., 1987, 52, p. 1835.

*Primary Examiner*—Paul F. Shaver
*Attorney, Agent, or Firm*—Mark L. Rodgers; William F. Marsh; James C. Simmons

[57] ABSTRACT

A process is provided for making metallated and substituted alkynes from feedstocks which include alkadienes containing allenic unsaturation or such alkadienes in a mixture with alkynes having either internal or terminal unsaturation, such as a mixture of propadiene and propyne. This reaction involves an initial step in which the allenic hydrocarbon and any internal alkyne is isomerized and simultaneously the resultant terminal alkynes are metallated with an alkali metal. The reaction is carried out at relatively low temperatures in a suitable inert solvent such as diethylether. When metallation is complete the reaction mixture can be contacted directly with any suitable electrophile, such as a halo silane, for example, chlorotrimethylsilane, and the alkali metal on the terminal alkyne is replaced with the desired substituent. The products thus formed are useful as monomers for preparing polymers having a variety of properties, for example, as asymmetric membranes for gas separation.

8 Claims, No Drawings

PREPARATION OF METALLATED AND SUBSTITUTED ALKYNES

FIELD OF THE INVENTION

This invention relates to the simultaneous isomerization and metallation of allenic hydrocarbons. In another aspect, it relates to the metallation of a mixture of alkyne and allenic hydrocarbons in the presence of an allene isomerization catalyst. In yet another aspect, it relates to the conversion of these metallated products to substituted alkynes which can then be converted into useful polymers.

BACKGROUND OF THE INVENTION

Recent developments in the use of polymers of substituted alkynes have focused interest on the preparation of such monomers. For example, poly-1-(trimethylsilyl)-1-propyne is very attractive in preparing membranes for gas separations. The monomer is prepared by metallating propyne with butyllithium followed by reaction with chlorotrimethylsilane. The fact that propyne is very expensive has adversely affected the economics of these substituted acetylenic polymers. One approach to reduce the cost of such polymers and other derivatives of substituted alkynes has been to use an impure source of alkynes as a feedstock. This approach is illustrated in U.S. Pat. No. 3,752,848, Smith (1973), which describes making tetrolic acid (2-butynoic acid) by introducing carbon dioxide into a slurry of propynyl alkali metal, such as propynyl sodium, and then hydrolyzing the carbonated slurry. The patent states that the unrecovered product slurry produced by the method of U.S. Pat. No. 3,410,918, Beumel, et al. (1968) can be used as the source of the propynyl alkali metal compound after disappearance of the alkali metal particles and cooling to below 80° C. The '918 patent describes the preparation of propynyl sodium and propynyl lithium by reacting propyne with sodium or sodium/lithium dispersions. A mixture of propyne and allene in a weight ratio of about 1:1 to 4:1 is used as the feedstock and the allene remains relatively inert so as not to interfere with the propyne metalation. Some propyne is said to be hydrogenated to propane. The propyne/allene feedstock is cheaper than pure propyne.

The feedstock such as that referred to by the '918 patent is actually available commercially as a cutting fuel and is referred to as MAPP gas, having a composition of about 23 to 36% propyne, 18 to 28% propadiene and 1 to 8 wt. % propylene and butenes.

Although it is known that propadiene can be isomerized to propyne, this approach has not been used to increase the value of such mixed feedstocks. U.S. Pat. No. 3,671,605, Smith (1972) discloses isomerizing allenes into acetylenic isomers at temperatures of −10 to 100° C., using a catalyst of sodium or potassium reacted with alumina. Lithium is said to be inoperable. Alumina is reacted with molten alkali metal with agitation and under an inert gas blanket. The allene, such as propadiene, may be pure or mixed with its acetylenic isomer, for example, propyne. In either case the product is said to be an equilibrium mixture in which the acetylenic isomer predominates.

Dykh, et al., *Izv. Akad. Nauk SSSR. Ser. Khim.* (1978), 11, 2473, disclose that allene can be isomerized to methyl acetylene on metal oxide and zeolite catalysts. Various aluminas were used at temperatures of 20 to 350° C. Isomerization of methyl acetylene to allene also occurs and the kinetics of the forward and reverse reactions are discussed.

Khulbe, C. P.; Mann, R. S., *Can. J. Chem.* (1978) 56, 2791, disclose equilibrium constants for the isomerization of allene to methyl acetylene and discuss this reaction catalyzed with silica-supported cobalt and iron.

The isomerization of allenes is also disclosed in U.S. Pat. No. 4,036,904 Strope (1977) which describes purifying a 1,3-butadiene stream prior to catalytic cyclodimerization when the stream contains allenes which would poison the dimerization catalyst. Allene and 1,2-butadiene are converted to acetylenic compounds over a magnesium oxide catalyst at 85 to 355° C. Allene is converted to methylacetylene and 1,2-butadiene is converted to 2-butyne or 1,3-butadiene.

Brown, C. A.; Yamashita, A., *J. Am. Chem. Soc.*, (1975), 97, 891 disclose that potassium 3-aminopropylamide rapidly catalyzes the isomerization of alkynes having interior triple bonds to 1-alkynes. Macaulay, S. R. *Can. J. Chem.*, (1980), 58, 2567 discloses sodium aminopropylamide with somewhat higher temperatures is more effective than the reagent of Brown, et al. The materials studied were decyn-1-ol and its isomers. Abrams, S. R., *Can. J. Chem.*, (1982), 60, 1238 states that isomerizations reported by Brown and Yamashita can be carried out with catalysts which are sodium salts of 1,3-diaminopropane or 1,2-diamino ethane. Use of the reagents is disclosed for isomerizing acetylenic acids.

Abrams, S. R., *Can. J. Chem.*, (1984), 62, 1333 describes an improvement in the catalysis of triple bond migration in isomerizations to form terminal alkynes and alkynols over the earlier work with catalysts which were sodium salts of 1,2-diaminoethane or 1,3-diaminopropane. The improved catalysts are lithium salts of these compounds with the addition of sodium or potassium alkoxides, such as potassium tert-butoxide.

In summary, the conversion of alkadienes by isomerization to terminal acetylenes is well known and a variety of isomerization catalysts are available for this procedure. Such isomerization of allenes is also suggested in Wotitz, et al. *J. Org. Chem.* (1973) 38, 489 and by Abrams. et al., *J. Org. Chem.* (1987) 52, 1835.

SUMMARY OF THE INVENTION

We have now found that a process for making metallated 1-alkynes can be accomplished by reacting, in an inert solvent under low temperature conditions., i.e. less than about 50° C, for allene isomerization and alkyne metallation, an allenic hydrocarbon of 3 to 8 carbon atoms with an alkali metal and allene isomerization catalyst. The isomerization reactions involving allenic hydrocarbons and alkynes, such as propadiene and propyne, are equilibrium reactions that are reversible. In other words the catalysts which convert allenic hydrocarbons to alkynes having terminal unsaturation, also isomerize the terminally unsaturated alkyne to the feedstock hydrocarbons. By carrying out a simultaneous metallation in an inert solvent, such as ethyl ether, under mild conditions of temperature which previously have not been reported, e.g., below about 50° C., the 1-alkyne is metallated as it is formed and effectively removed from the equilibrium mixture. In this manner, for example, all of the $C_3H_4$ hydrocarbon in a propyne/propadiene feedstock, can be converted to metallated propyne which can then in turn be converted to a substituted propyne useful as a polymerization monomer. Terminal alkynes can also be present in the reaction mixture, in which case they are metallated at said low temperature conditions, which heretofor have not been reported in the prior art.

The invention also includes making substituted alkynes by first reacting in an inert solvent under conditions for allene isomerization an allenic hydrocarbon having 3 to 8 carbon atoms with an alkali metal and allene isomerization catalyst, thereby forming a metallated 1-alkyne and thereafter allowing the mixture to react with an electrophile, leaving a substituent on the alkyne.

DETAILED DESCRIPTION OF THE INVENTION

Substituted alkynes having 3 to 8 carbon atoms per molecule, and particularly substituted propynes, are monomers which can be converted into polymers possessing a variety of useful properties. These polymers tend to be very expensive, however, in part because of the high cost of the alkyne which is used to prepare the monomer. The present invention provides a convenient, low cost procedure which can be carried out in two steps in one reaction vessel without intermediate reaction work-up to obtain substituted alkynes, particularly propynes, from inexpensive feedstocks, such as the commercially available MAPP gas, which contains both propyne and propadiene. The procedure of the invention converts both of these unsaturated hydrocarbons to the desired substituted alkyne, first by a simultaneous isomerization/metallation reaction and subsequently by substitution of the metal with a suitable electrophile that can react with the alkynylmetal species.

The isomerization reactions involving allenic hydrocarbons and alkynes, such as propadiene and propyne, are equilibrium reactions that are reversible. In other words the catalysts which convert allenic hydrocarbons to alkynes having terminal unsaturation, also isomerize the terminally unsaturated alkyne to the feedstock hydrocarbons. By carrying out a simultaneous metallation in an inert solvent, such as ethyl ether, under mild conditions of temperature which previously have not been reported, e.g., below about 50° C., the 1-alkyne is metallated as it is formed and effectively removed from the equilibrium mixture. In this manner, for example, all of the $C_3H_4$ hydrocarbon in a propyne/propadiene feedstock, can be converted to metallated propyne which can then in turn be converted to a substituted propyne useful as a polymerization monomer. The fact that the entire procedure can be carried out in one reaction vessel also offers economic advantages in reducing the costs of equipment and operations.

In accordance with the present invention, a substituted alkyne having the general structural formula:

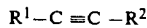

$$R^1-C \equiv C-R^2$$

where $R^1$ is alkyl or aralkyl having 1 to 8 carbons and $R^2$ is a silyl. germyl, alkanol or alkanone substituent, is produced in a solvent, preferably diethyl ether, according to a two step, one-pot procedure. Examples of alkynes which can be so substituted include methylacetylene, ethylacetylene, pentyne-1, 3-methylbutyne-1, hexyne-1, 3-phenyl-1-propyne and the like.

The first step, for example, involves metallation/isomerization of a propyne/propadiene mixture in the presence of an alkali metal, preferably sodium, and one of the following catalysts: either an alkyl amine, preferably an alkyl diamine, more preferably 1,3-diaminopropane in combination with an alkali metal base such as a hydride or an alkoxide; or a metal oxide, preferably magnesium oxide. This is followed by reaction of the intermediate propynylmetal derivative with any suitable electrophile RX where X may be a leaving group such as Cl, Br, I and the like. Alternatively, the propynylmetal derivative can be combined with an unsaturated group (e.g., carbonyl) which can undergo reduction via reaction with the propynylmetal species.

In a typical reaction, 1.0 molar equiv. of sodium metal is combined with the appropriate amount of isomerization agent, either 0.02 to 5.0 equiv. of magnesium oxide, or 0.02 to 1.0 equiv. of 1,3-diaminopropane in the presence of an additional alkali metal base such as a hydride or alkoxide, in diethyl ether and the mixture is cooled to between −40° and −70° C. The $C_3H_4$ hydrocarbon gas stream (1.0 to 2.0 molar equiv. of the reactive component(s)) is introduced all at once and the mixture is allowed to warm gradually to room temperature over 1 to 3 hours, continually recondensing the volatile hydrocarbon into the ethereal solution by means of a dry ice/isopropanol condenser. The resultant propynylsodium slurry is then treated with (1.0 to 2.0 molar equiv.) of the electrophile. Time and temperature for complete reaction with the electrophile is dependent upon electrophile structure. The following examples illustrate that propadiene portions of a $C_3H_4$ hydrocarbon feedstock afford substituted propynes under the given conditions.

EXAMPLE 1

Magnesium oxide (2.2 g; vacuum oven dried at 400° C. for several hours) and freshly prepared sodium metal (0.6 g; finely divided) were combined in 25 ml of diethyl ether (distilled from $CaH_2$) and cooled to −40° C. Pure propadiene (1.5 g) was introduced and the mixture was allowed to warm to room temperature with stirring for an additional 2 hours. Benzyldimethylchlorosilane (4.4 g) was added all at once and the reaction was allowed to proceed at room temperature for 15 hours. Aqueous 10% HCl was added dropwise to destroy any residual sodium metal. The product was then extracted with pentane and concentrated to afford 3.6 g (80%) of crude benzyldimethylsilylpropyne. The purity of the crude propyne product was high as indicated by $^1H$ NMR.

EXAMPLE 2

Sodium metal (0.6 g; finely divided), 1,3-diaminopropane (0.1 g; freshly distilled), and potassium hydride (0.05 g) were combined in 25 ml of diethyl ether (distilled from $CaH_2$) and cooled to −70° C. Pure propadiene (2.0 g) was introduced and the mixture was allowed to warm to room temperature with stirring for an additional 2 hours. Benzyldimethylchlorosilane (4.4 g) was added all at once and the reaction was allowed to proceed at room temperature for 15 hours. Aqueous 10% HCl was added dropwise to destroy any residual sodium metal. The product was then extracted with pentane and analyzed by gas chromatograph (GC) /mass spectrometry (MS). Results showed the product to be benzyldimethylsilylpropyne and no allenic product was observed.

EXAMPLE 3

A run was carried out to demonstrate the metallation of propyne at low temperatures. Sodium metal (1.1 g; freshly cut to expose clean surface) was cooled to −78° C. in 50 ml of diethyl ether. Propyne (7.5 g, 0.19 mol)

was introduced and the reaction mixture was allowed to warm and stir at room temperature for an additional 3 h. Benzyldimethylchlorosilane (8.8 g, 0.048 mol) was added dropwise over 15 min and the reaction was allowed to proceed for an additional 15 h. Water (50 ml) was added to destroy any residual sodium metal, the product was extracted with three 50 ml portions of pentane, then concentrated and dried to afford 9.1 g of crude benzyldimethylsilylpropyne. The purity of the crude product was very high as indicated by $^1$H NMR.

Examples 4 and 5 describe the procedure for the synthesis of 1-(trimethylsilyl)-1-propyne, a monomer of interest because of its polymer, poly-1-(trimethylsilyl)-1-propyne.

ILLUSTRATIVE EXAMPLE 4

Sodium metal (0.6 g; finely divided) is combined with magnesium oxide (2.2 g; vacuum oven dried at 400° C. for several hours) in 25 mL of diethyl Other (distilled from CaH$_2$) and the mixture is cooled to −40 C. The propadiene/propyne gas mixture (2.0 g; containing about 70% C$_3$H$_4$ hydrocarbon) is introduced all at once and the mixture is allowed to warm gradually to room temperature over 1 hour, continually recondensing the volatile hydrocarbon into the ethereal solution by means of a dry ice/isopropanol condenser. The resultant propynylsodium slurry is then treated with chlorotrimethylsilane (3.1 g) and the reaction is allowed to proceed at room temperature for 15 hours. Aqueous 10% HCl is added dropwise to destroy any residual sodium metal. The product is then extracted with pentane and the organic extract distilled with careful fractionation to obtain 1-(trimethylsilyl)-1-propyne.

ILLUSTRATIVE EXAMPLE 5

The procedure of Example 3 is repeated using 1,3-diaminopropane (0.1 g) and potassium hydride (0.05 g) as the isomerization catalyst instead of magnesium oxide.

These examples give representative catalysts, reagents and reaction solvents for the preparation of substituted alkynes from alkyne/alkadiene/ hydrocarbon mixtures and are not meant to be limiting in any way.

A wide variety of electrophiles will react with the intermediate propynylmetal species. The appropriate choice of electrophile depends upon the structure of the desired product. For example, just as 1-(trimethylsilyl)-1-propyne is prepared according to the procedure set forth in Examples 4 and 5 by the addition of chlorotrimethylsilane to the propynylsodium slurry, a number of other acetylenic monomers (e.g., 1-(ethyldimethylsilyl)-1-propyne, 1-(phenyldimethylsilyl)-1-propyne, 1-(trimethylgermyl)-1-propyne as well as 2-butyn-4-ols and alkyl substituted propynes can be prepared by treatment of the propynylmetal derivative with the appropriate halosilane or germane, aldehyde, ketone, or alkyl halide.

In addition to the use of sodium as a metallating agent, other alkali metals (e.g., lithium, potassium) are also effective.

Aromatic hydrocarbon solvents such as benzene, toluene, xylene, or ethylbenzene, aliphatic hydrocarbons such as hexane or octane and ethereal solvents including tetrahydrofuran, dioxane, ethylene glycol dimethyl ether and ethylene glycol diethyl ether can be used instead of diethyl ether as the reaction solvent.

A variety of primary and secondary amines and diamines will isomerize alkadienes to alkynes in the presence of an alkali metal hydride or alkoxide. Suitable isomerization catalysts include 1,3-diaminopropane, alkylamines such as methylamine and dimethylamine, alkyl diamines such as 1,2-diaminoethane, 1,2-diaminopropane, 1,4-diaminobutane and 1,2-diaminocyclohexane, aryl amines such as aniline, and aryl diamines such as 1,2-, 1,3- or 1,4-phenylene diamine, and the like.

Also useful as the isomerization catalyst are magnesium oxide and other Group IIA (alkaline earth) oxides (e.g., CaO) as well as Group IIIB (e.g., La$_2$O$_3$) and Group IVB (e.g., ZrO$_2$) oxides. Additional alternatives include the above oxides and those of Groups IIIA and IVA (e.g.., Al$_2$O$_3$, SiO$_2$) treated with alkali metals or alkali metal salts such as hydroxides and carbonates. See Tanabe, K., "Solid Acids and Bases", Kodansha, Tokyo. Academic Press, New York, 1970 and Pines, H.; Stalick, H. M., "Base Catalyzed Reactions of Hydrocarbons and Related Compounds", Academic Press, New York, 1977 for comprehensive reviews of suitable solid state isomerization catalysts.

Other aspects and embodiments of our invention will be apparent to those skilled in the art from the foregoing disclosure without departing from the spirit or scope of the invention.

We claim:

1. A process for making metallated 1-alkynes which comprises contacting in an inert solvent under conditions for allene isomerization an allenic hydrocarbon of 3 to B carbon atoms with an alkali metal in the presence of an allene isomerization catalyst, thereby forming a metallated 1-alkyne.

2. The process of claim 1 wherein an alkyne of 3 to 8 carbon atoms is added to the reaction mixture either separately or with said allenic hydrocarbon.

3. The process of claim 2 wherein the feed for the reaction is a hydrocarbon mixture containing both said alkyne and said allenic hydrocarbon.

4. The process of claim 1 wherein said isomerization catalyst is an oxide of a metal of Groups IIA, IIIB or IVB of the Periodic Table.

5. The process of claim 1 wherein said isomerization catalyst is an oxide of a metal of Groups IIA, IIIA, IVA, IIIB or IVB of the Periodic Table previously treated with an alkali metal or alkali metal salt.

6. The process of claim 5 wherein said oxide is a compound of magnesium, calcium, lanthanum, zirconium, aluminum, silicon or mixtures thereof.

7. The process of claim 1 wherein said isomerization catalyst is an alkyl or aryl amine in the presence of an alkali metal compound.

8. The process of claim 1 wherein said reaction is carried out at temperatures below 50° C.

* * * * *

UNITED STATES PATENT AND TRADEMARK OFFICE
CERTIFICATE OF CORRECTION

PATENT NO. : 5,062,998

DATED : November 5, 1991

INVENTOR(S) : Frederick L. Herman, et al

It is certified that error appears in the above-identified patent and that said Letters Patent is hereby corrected as shown below:

Column 6, Line 37
    Delete "B" and substitute therefore -- 8 --

Signed and Sealed this

Twenty-sixth Day of October, 1993

Attest:

BRUCE LEHMAN

Attesting Officer

Commissioner of Patents and Trademarks